(12) United States Patent
Lee et al.

(10) Patent No.: US 7,846,700 B2
(45) Date of Patent: Dec. 7, 2010

(54) METHOD FOR PREPARING TRANSFORMANTS EXPRESSING BENZALDEHYDE DEHYDROGENASE AND PREPARATION OF 2,6-NAPHTHALENE DICARBOXYLIC ACID USING THE TRANSFORMANTS

(75) Inventors: Jong Hwan Lee, Gyeonggi-Do (KR); Yong Bok Choi, Gyeonggi-Do (KR)

(73) Assignee: Hyosung Corporation, Seoul (KR)

( * ) Notice: Subject to any disclaimer, the term of this patent is extended or adjusted under 35 U.S.C. 154(b) by 74 days.

(21) Appl. No.: 11/720,052

(22) PCT Filed: Dec. 23, 2005

(86) PCT No.: PCT/KR2005/004486

§ 371 (c)(1), (2), (4) Date: Feb. 27, 2008

(87) PCT Pub. No.: WO2006/071028

PCT Pub. Date: Jul. 6, 2006

(65) Prior Publication Data

US 2009/0035817 A1    Feb. 5, 2009

(30) Foreign Application Priority Data

Dec. 30, 2004  (KR) .................. 10-2004-0116687

(51) Int. Cl.
- C12P 7/62 (2006.01)
- C12P 7/40 (2006.01)
- C12P 21/06 (2006.01)
- C12N 1/20 (2006.01)
- C12N 9/06 (2006.01)

(52) U.S. Cl. ............... 435/135; 435/136; 435/252.3; 435/191; 435/69.1

(58) Field of Classification Search .......... 435/135, 435/136, 252.3, 191, 69.1
See application file for complete search history.

(56) References Cited

U.S. PATENT DOCUMENTS

| | | | |
|---|---|---|---|
| 5,728,870 A | 3/1998 | Holzhauer et al. | |
| 5,872,284 A | 2/1999 | Iwasaki et al. | |
| 6,114,575 A | 9/2000 | McMahon et al. | |
| 6,187,569 B1 * | 2/2001 | Bramucci et al. | 435/136 |
| 6,756,509 B2 | 6/2004 | Nagase et al. | |
| 2002/0173674 A1 | 11/2002 | Rao et al. | |
| 2003/0233675 A1 * | 12/2003 | Cao et al. | 800/279 |
| 2004/0106177 A1 | 6/2004 | Schmid et al. | |

FOREIGN PATENT DOCUMENTS

| | | |
|---|---|---|
| JP | 07 079768 A | 3/1995 |
| JP | 2000 106878 | 4/2000 |
| KR | 10 2004 0060351 | 7/2004 |
| KR | 10 2004 0061548 | 7/2004 |
| WO | WO 03/068735 A2 | 8/2003 |

OTHER PUBLICATIONS

Romine et al. Complete sequence of 184-Kilobase catabolic plasmid from *Sphingomonas aromaticivorans* F199. J. Bacteriol., 1999, vol. 181 (5): 1585-1602.*

Bramucci et al., Biotransformation of p-xylene and 2,6-dimethylnapthalene by xylene monoxygenase cloned from a *Sphingomonas* isolate. Appl Microbiol Biotechnol., 2002, vol. 59: 679-684.*

Peng et al., "Characterization of *Sphingomonas* aldehyde dehydrogenase catalyzing the conversion of various aromatic aldehydes to their carboxylic acids," *Appl Microbiol Biotechnol*, 2005, vol. 69, pp. 141-150.

Kim, S., et al., "Benzaldehyde dehydrogenase," NCBI Database, Accession No. Q9Z3W8, May 1, 1999.

* cited by examiner

*Primary Examiner*—Ganapathirama Raghu
(74) *Attorney, Agent, or Firm*—Saliwanchik, Lloyd & Saliwanchik

(57) ABSTRACT

Disclosed herein are a method for preparing a transformant which carries a gene encoding benzaldehyde dehydrogenase derived from *Sphingomonas aromaticivorans* KCTC 2888 and expresses the enzyme, and biological purification of the crude naphthalene dicarboxylic acid, obtained upon the oxidation of 2,6-dimethylnaphthalene with the concomitant production of 2-formyl-6-naphthoic acid, by applying a transformant for the conversion of FNA into naphthalene dicarboxylic acid.

4 Claims, 2 Drawing Sheets

SEQUENCE LISTING

```
<160> NUMBER OF SEQ ID NOS: 3

<210> SEQ ID NO 1
<211> LENGTH: 1506
<212> TYPE: DNA
<213> ORGANISM: Sphingomonas aromaticivorans

<400> SEQUENCE: 1
atggctacgc agttgagaag tgcagaaaac gaatacggga tcaagtccga gtacggccac      60
tatatcggcg gcgagtggat cgccggggac agcggcaaga ccatcgatct gctcaatccc     120
tcgaccggca aggtgctgac caagattcag gccggcaacg ccaaggatat cgaacgcgcg     180
attgccgccg ccaaggcggc gtttcccaag tggtcgcaga gctgcccgg cgagcgccaa      240 gaaatcctga tcgaggttgc gcgtcgtctg aaggcacgcc attcgcacta tgccaccctc     300
gaaacgctca caacggcaa gccgatgcgc gaatcgatgt atttcgatat gccgcagacg      360
atcgggcagt ttgagctgtt cgccggtgcc gcctatggcc tgcacggcca gacgctcgat     420
tatcccgacg cgatcggcat cgtccaccgc gaaccgctcg gcgtctgcgc gcagattatc     480
ccatggaacg tgccgatgtt gatgatggcg tgcaagatcg cgcccgcgct ggcctcgggc     540
aacactgtcg ttctgaagcc ggccgaaacg gtctgccttt cggtgattga attcttcgtg     600
gaaatggctg atctgttgcc gccgggtgtg atcaacgtcg tcaccggcta tggcgcggac     660
gtgggcgagg cgctggtcac cagccccgat gtcgccaagg tggccttcac cggttcgatc     720
gccaccgcgc gccggatcat ccagtatgcc tcggccaaca tcatccccca gacgctcgag     780
ttgggcggca agtcggcgca catcgtgtgt ggcgatgccg acatcgacgc ggcggtggaa     840
agcgcgacta tgtcgaccgt gctcaacaag ggcgaagtct gtctggccgg ttcgcgcctg     900
ttcctgcacc agtcgatcca ggacgagttc ctggccaagt tcaagaccgc gcttgaaggc     960
atccgccagg gcgacccgct cgacatggcg acccagcttg gcgcccaggc atcgaagatg    1020
cagtttgaca aggtgcaaag ctacctgcgc ctggccaccg aggaagggc cgaggtcctg    1080
```

-continued

```
accggcggca gccgctcgga tgccgcagat ctggccgatg gcaattttat caagccgacc    1140
gtgttcacca acgtcaacaa ctccatgcgg atcgcgcagg aagagatctt cggaccggtt    1200
accagcgtca tcacctggag cgacgaagac gacatgatga agcaggccaa caatacaact    1260
tacggcctcg ctggcggcgt ctggaccaag gacatcgccc gagcccaccg gattgcgcgc    1320
aagctcgaaa ctggcacggt ctggatcaat cgctactaca acctgaaggc caacatgccg    1380
ctgggcggtt acaagcaaag cggcttcggg cgtgaattca gccatgaagt gctgaatcac    1440
tacacccaga ccaagtcggt ggtggtcaac ctccaggaag gtcgcaccgg aatgttcgat    1500
cagtga                                                                1506

<210> SEQ ID NO 2
<211> LENGTH: 24
<212> TYPE: DNA
<213> ORGANISM: Sphingomonas aromaticivorans

<400> SEQUENCE: 2
ggagaattca tatggctacg cagt                                              24

<210> SEQ ID NO 3
<211> LENGTH: 24
<212> TYPE: DNA
<213> ORGANISM: Sphingomonas aromaticivorans

<400> SEQUENCE: 3
gtcttgcagt gagctcgttt ctcc                                              24
```

METHOD FOR PREPARING TRANSFORMANTS EXPRESSING BENZALDEHYDE DEHYDROGENASE AND PREPARATION OF 2,6-NAPHTHALENE DICARBOXYLIC ACID USING THE TRANSFORMANTS

CROSS-REFERENCE TO A RELATED APPLICATION

This application is a National Stage Application of International Application Number PCT/KR2005/004486, filed Dec. 23, 2005; which claims priority to Korean Application No. 10 2004 0113981, filed Dec. 30, 2004.

TECHNICAL FIELD

The present invention relates to a method for preparing a transformant which carries a gene encoding benzaldehyde dehydrogenase derived from *Sphingomonas aromaticivorans* KCTC 2888 and expresses the enzyme and the use of the transformant in purifying crude naphthalene dicarboxylic acid (hereinafter referred to as "cNDA"), which is obtained upon the oxidation of 2,6-dimethylnaphthalene (hereinafter, referred to as "2,6-DMN") with the concomitant production of 2-formyl-6-naphthoic acid (hereinafter referred to as "FNA"), at high purity by converting FNA into 2,6-naphthalene dicarboxylic acid (hereinafter referred to as "NDA").

BACKGROUND ART

Diesters of naphthalene dicarboxylic acid find general and useful application in the preparation of high performance polymeric materials, such as polyesters and polyamides. Of the diesters, dimethyl-2,6-naphthalene dicarboxylate (hereinafter, referred to as "NDC") is taken as representative. Poly(ethylene-2,6-naphthalene) (hereinafter, referred to as "PEN"), one such high performance polyester, is prepared by the condensation of NDC with ethylene glycol. Fibers and films made from PEN are found to have advantages in terms of strength and thermal properties over poly(ethylene terephthalate) (hereinafter, referred to as "PET"). Thanks to its excellent physical properties, PEN is used to form thin films useful in the preparation of magnetic recording tapes and electromagnetic parts. In addition, because of its superior resistance to gas diffusion, and particularly to the diffusion of carbon dioxide, oxygen and water vapor, films made from PEN are applicable for manufacturing food containers, particularly "hot fill" type food containers. Also, PEN can be used to make high strength fibers useful in the preparation of tire cord.

Nowadays, NDC, as shown in FIG. 1, is generally produced by oxidizing DMN into crude naphthalene dicarboxylic acid (cNDA), followed by esterification. In most current cases, NDC is used as a main material for the synthesis of PEN. However, NDC suffers from several problems, compared to NDA. First, NDC is condensed into PEN with the concomitant production of methanol, which carries a danger of explosion, while water is produced upon the condensation of NDA. Next, because it is obtained from NDA by esterification and purification, NDC requires one more process compared to NDA. Also, NDC cannot take advantage of PET production facilities that may already exist. Despite such disadvantages, NDC is usually used, instead of NDA, for the synthesis of PEN because NDA has not been prepared with sufficient purity for use in the synthesis of PET.

The oxidation of DMN leads to cNDA, with by-products, such as 2-formyl-6-naphthoic acid, 2-naphthoic acid, etc., concomitantly produced as a result of incomplete oxidation, as seen in FIG. 2. The impurities, particularly, FNA, if present, cause breaks during the polymerization of PEN into polymeric materials, thereby having a bad influence on the properties of the polymers. To apply cNDA for the synthesis of PEN, FNA must be removed therefrom in advance, but it is difficult.

There are various methods known to remove FNA from cNDA reactions. For example, recrystallization for purifying NDA, a repetition of oxidation, and conversion of cNDA into NDC in the presence of methanol, followed by either hydration or hydrogenation into purified NDA have been proposed. Additionally, attempts have been made to remove FNA by solvent washing, melt crystallization, high pressure crystallization, supercritical extraction, etc. However, these techniques just account for NDA with insufficient purity. On the other hand, conventional methods can increase the purity of NDA, except making a sacrifice of yield, so that they are difficult to apply in practice.

As described above, chemical or physical methods for NDA production are given problems, including the production of environmental pollution, the likelihood of explosions due to high temperatures and pressures, an increase in production costs due to large-scale facilities, large energy consumption, etc. For direct use in polymerization to high performance polymeric material, 2,6-naphthalene dicarboxylic acid must be of high purity, which is difficult to attain with conventional methods. An additional purification process, even if capable of achieving the high purity in NDA, gives rise to productivity reduction and process extension.

Thus, extensive attention has recently been paid to biological methods, especially using microorganisms. Previously, the present inventors developed FNA removal using a novel *Bacillus* sp. as disclosed in Korean Pat. Appl'n No. 2002-0087819 and proposed a method for preparing aromatic aldehydes and carboxylic acids in the presence of xylene monooxygenase as disclosed in Korean Pat. Appl'n No. 2002-7005344. Nowhere is the conversion of FNA into NDA using benzaldehyde dehydrogenase derived from *Sphingomonas aromaticivorans* described in the previous literature.

DISCLOSURE OF THE INVENTION

Accordingly, the present invention has been made keeping in mind the above problems occurring in the prior art, and an object of the present invention is to provide a method for preparing transformants expressing benzaldehyde dehydrogenase, encoded by an xylC gene, that can be used for the purification of NDA.

Another object of the present invention is to provide a method for purifying cNDA, in which FNA contained in cNDA is oxidized into NDA in the presence of the transformant.

In accordance with one aspect of the present invention, a method comprising constructing a recombinant expression vector carrying the gene of SEQ ID NO: 1 encoding benzaldehyde dehydrogenase (xylC) derived from *Sphingomonas aromaticivorans* KCTC 2888, and transforming the host cell with the recombinant expression vector is provided for preparing a transformant expressing benzaldehyde dehydrogenase.

In accordance with another aspect of the present invention, the transformant prepared by the method, is provided.

In accordance with a further aspect of the present invention, a method comprising culturing the transformant at 25 to 45° C., and adding IPTG in an amount from 0.1 to 2.0 mM to the transformant culture to induce the expression of benzaldehyde dehydrogenase is provided for producing benzaldehyde dehydrogenase.

In accordance with still a further aspect of the present invention, a method comprising reacting the crude naphthalene dimethylcarboxylic acid with the transformant to convert the 2-formyl-6-naphthoic acid contained within the crude naphthalene dimethylcarboxylic acid into 2,6-naphthalene dicarboxylic acid is provided for purifying crude naphthalene dimethylcarboxylic acid.

BRIEF DESCRIPTION OF THE DRAWINGS

The above and other objects, features and advantages of the present invention will be more clearly understood from the following detailed description taken in conjunction with the accompanying drawings, in which.

BEST MODE FOR CARRYING OUT THE INVENTION

A detailed description will be given of the present invention, below.

In accordance with an aspect of the present invention, a method is provided for preparing transformants expressing benzaldehyde dehydrogenase. For this purpose, xylC, a gene coding for benzaldehyde dehydrogenase, is cloned from *Sphingomonas aromaticivorans* and inserted into a recombinant expression vector, followed by the introduction of the vector into a suitable host cell.

Benzaldehyde dehydrogenase (BZDH), is a homodimer and is encoded by the xylC gene. Using *E. coli* which is genetically engineered to express xylC, benzaldehyde, 3-methylbenzaldehyde, 4-methyl benzaldehyde, 3-nitrobenzaldehyde and chlorine-substituted benzaldehyde can be oxidized (refer to: Inoue et al., *J. Bacteriol.*, 177: 1196-1201, 1995).

Cloning of the xylC gene, expressed as SEQ ID NO: 1 and coding for benzaldehyde dehydrogenase, is achieved with *Sphingomonas aromaticivorans*. In order to clone the xylC gene, polymerase chain reaction (PCR) is performed using a set of primers 5'-GGAGAATTCATATGGCTACGCAGT-3' (SEQ ID NO: 2) and 5'-GTCTTGCAGTGAGCTCG-TTTCTCC-3' (SEQ ID NO: 3) synthesized on the basis of xylC, with the plasmid DNA (pNL1) from *Sphingomonas aromaticivorans* (KCTC 2888) serving as a template.

Transformants expressing benzaldehyde dehydrogenase are created with a recombinant expression vector carrying the xylC gene (SEQ ID NO: 1). The recombinant expression vector can be obtained by functionally linking the cloned xylC gene to a promoter.

Figure 1:
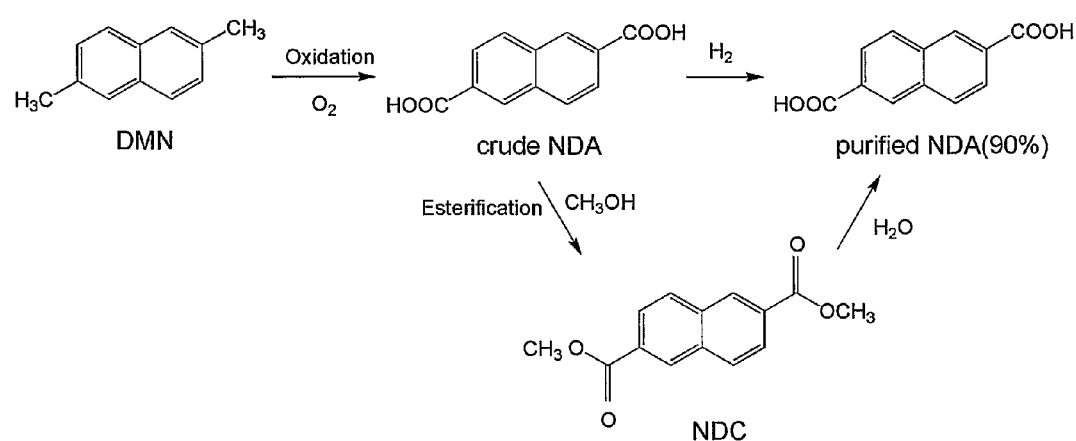
FIG. 1 is a reaction scheme showing the conversion of 2,6-dimethyl naphthalene into naphthalene dicarboxylic acid and naphthalene dicarboxylate by a conventional oxidation method.
Figure 2:
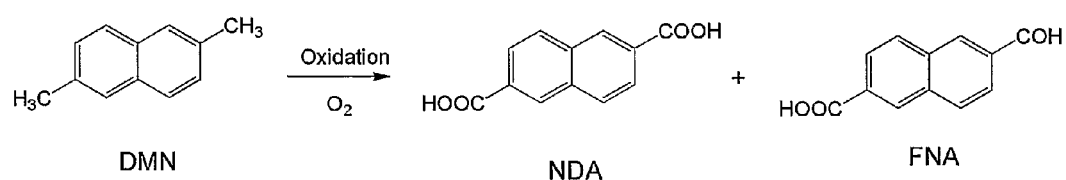
FIG. 2 is a reaction scheme showing the oxidation of 2,6-dimethyl naphthalene into 2,6-naphthalene dicarboxylic acid with the concomitant production of 2-formyl-6-naphthoic acid.
Figure 3:
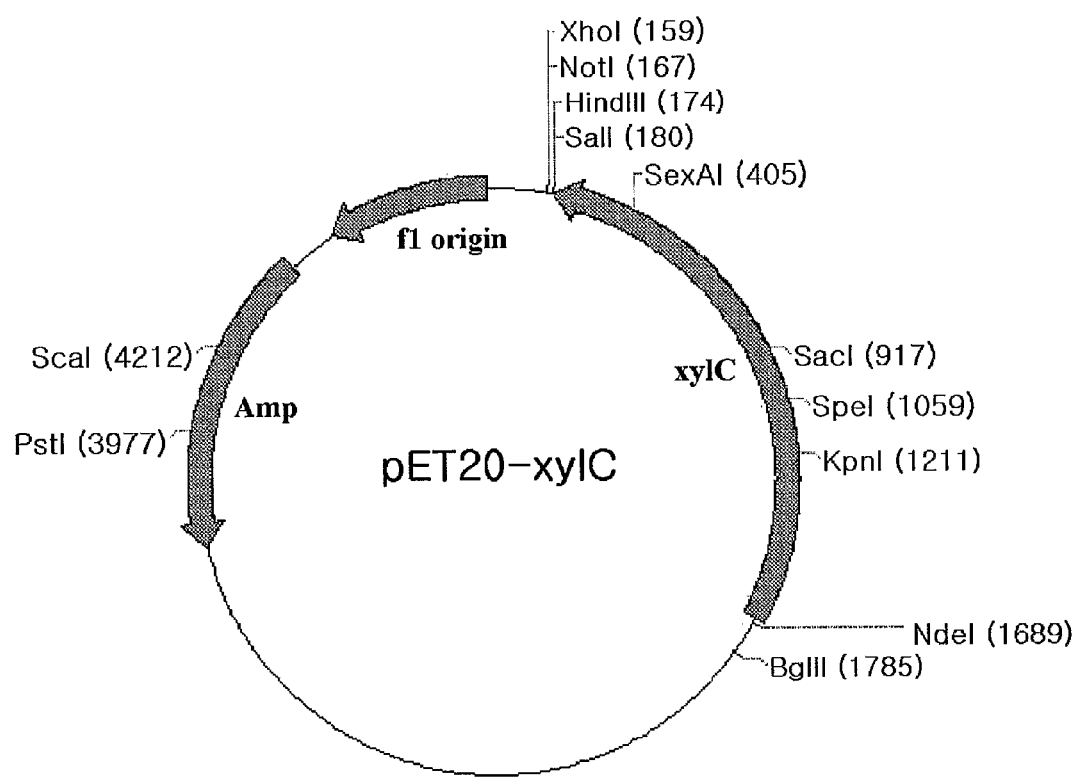
FIG. 3 is a gene map of the recombinant expression vector pET20-xylC carrying a gene encoding benzaldehyde dehydrogenase derived from *Sphingomonas aromaticivorans*.

With reference to FIG. 3, there is a gene map of the recombinant expression vector pET20-xylC carrying a gene encoding benzaldehyde dehydrogenase derived from *Sphingomonas aromaticivorans*. As seen in FIG. 3, a DNA fragment about 1.5 kbp long, expressed as SEQ ID NO: 1, is inserted into a pET-20b(+) vector to form the recombinant vector pET20-xylC.

As disclosed and claimed herein, the sequence set forth in SEQ ID NO: 1, coding for xylC derived from *Sphingomonas aromaticivorans* (KCTC 2888), is intended to include "conservative sequence modifications", i.e., nucleotide and amino acid sequence modifications that do not significantly affect or alter the catalytic characteristics of the enzyme encoded by the nucleotide sequence or containing the amino acid sequence. Such conservative sequence modifications include nucleotide and amino acid substitutions, additions and deletions. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain.

Expression vectors useful in the present invention are not specifically limited. Any expression vectors well known in the art may be available, including, for example, pForexT vectors, pUC vectors, pBluescript vectors, pET vectors, etc., with a T7 promoter, a T3 promoter, or an Sp6 promoter.

The preparation of transformants can be accomplished using recombinant expression in a manner well known in the art. In accordance with the present invention, 2-formyl-6-naphthoic acid is converted into 2,6-naphthalene dicarboxylic acid with the help of the microorganism transformed with the expression vector of benzaldehyde dehydrogenase. Accordingly, it is preferred that the transformed microorganism be able to express benzaldehyde dehydrogenase at a high level. In the case of a pET-20b(+) vector, the expression of structural genes is regulated under the control of a T7 promoter, so that it can be induced with isopropyl-β-D-thiogalactopyranoside (hereinafter referred to as "IPTG").

Suitable as a host cell for the preparation of the transformants are enteric bacteria, such as MC1061 (*E. coli*), JM109 (*E. coli*), XL1-Blue (*E. coli*), and DH5α (*E. coli*). The expression vector may be introduced into the host cell using a heat shock, electroporation, microinjection, or particle bombardment method, which is not intended to limit the present invention.

In the meanwhile, the cloning of the xylC gene into the expression vector may be confirmed through digestion with restriction enzymes or base sequencing.

The transformant is sufficiently grown at a temperature from 25 to 45° C. and preferably at 37° C. and is then inoculated in 100 ml of an LB medium in an amount of 1% (v/v). When an OD600 from 0.4 to 0.5 is observed, IPTG is added in an amount from 0.1 to 2.0 mM and preferably in an amount of 0.5 mM to induce the expression of benzaldehyde dehydrogenase, followed by incubation at 37° C. It should be noted that the transformant growth and the protein expression may be achieved by any of the methods known in the art and are not limited to that described above.

According to the present invention, crude naphthalene dimethylcarboxylic acid can be purified by converting the 2-formyl-6-naphthoic acid contained in the crude into 2,6-naphthalene dicarboxylic acid with the help of the transformed microorganism in which benzaldehyde dehydrogenase is expressed at a high level.

For use in application for the conversion, the biomass of the transformed microorganism recovered from the culture is suspended in physiological saline.

In the presence of the enzyme, conversion to 2,6-naphthalene dicarboxylic acid from the 2-formyl-6-naphthoic acid contained in the crude naphthalene dimethylcarboxylic acid is allowed to occur in a buffer at a pH from 6.0 to 10.0, and preferably at pH 8.0.

Examples of the buffer useful for the enzymatic conversion include a sodium carbonate buffer ($Na_2CO_3/NaHCO_3$), a glycine buffer (glycine/NaOH), a potassium phosphate buffer ($KH_2PO_4/KOH$, $K_2HPO_4/KOH$, $KH_2PO_4/NaOH$, $K_2HPO_4/NaOH$) a sodium phosphate buffer ($Na_2HPO_4/NaH_2PO_4$), a succinic acid buffer (succinic acid/NaOH), a sodium acetate buffer (sodium acetate/acetic acid), a citric acid buffer (citric acid/sodium citrate), a sodium pyrophosphate buffer ($Na_4P_2O_7$/HCl), a boric acid buffer (boric acid/NaOH), and a sodium borate buffer (sodium borate/HCl), with preference for phosphate buffers, in terms of enzymatic activity.

Optionally, an organic solvent may be added to the enzyme reaction so as to dissolve cNDA. Examples of suitable organic solvents include dimethylsulfoxide (DMSO), N,N-dimethylformamide (DMF), N,N-dimethylacetamide (DMA), and tetrahydrofuran (THF) with 5% DMSO being preferred in terms of enzymatic activity. Preferably, the amount of the organic solvent does not exceed 20% of the total weight of the reactants.

The conversion is preferably carried out from 25 to 45° C. and most preferably at 30° C. to optimize the reaction rate. As for the reaction time period sufficient to convert 2-formyl-6-naphthoic acid to 2,6-naphthalene dicarboxylic acid, it ranges from 0.5 to 48 hours, preferably from 0.5 to 24 hours and, is more preferably 6 hours.

The transformant XL1-Blue(pET20-xylC) is inoculated in an LB media containing 1,000 ppm of cNDA and 100 mg/L of ampicillin and incubated at 37° C. for a sufficient time period with stirring. HPLC analysis of the supernatant indicated that the benzaldehyde dehydrogenase (xylC) expressed removed FNA to produce 2,6-NDA at high purity.

A better understanding of the present invention may be obtained through the following examples which are set forth to illustrate, but are not to be construed as the limit of the present invention.

EXAMPLE 1

Cloning of xylC Gene

In order to clone an xylC gene coding for benzaldehyde dehydrogenase from *Sphingomonas aromaticivorans* (KCTC 2888), the plasmid (pNL1) carrying the xylC gene was first isolated therefrom (refer to: Sambrook et al., Molecular Cloning, A Laboratory Manual 2nd Ed., Cold Spring Harbor Laboratory Press, Cold Spring Harbor, N.Y., 1989). For PCR using the isolated plasmid DNA (pNL1) as a template, primer 1,5'-GGAGAATTCATATGGCTACGCAGT-3' (SEQ ID NO: 2) and primer 2, 5'-GTCTTGCAGTGAGCTCGTTTCTCC-3' (SEQ ID NO: 3) were synthesized based on the public DNA base sequence of xylC (available from GenBank Sequence Database, NC 002033). Using the set of primers, PCR for cloning a full length xylC gene started with pre-denaturation for 5 min at 94° C. and was carried out with 40 cycles of denaturing temperature at 94° C. for 1 min, annealing temperature at 56° C. for 1 min and extending temperature at 72° C. for 1.5 min, finally followed by 72° C. extension for an additional 10 min. From the PCR reaction, a DNA fragment about 1.5 kbp long was isolated, and digested with NdeI and SalI. This was inserted into the plasmid pET-20b(+) which was already cut with the same restriction enzymes, so as to construct the recombinant expression vector pET20-xylC as shown in FIG. 3.

EXAMPLE 2

Analysis of Cloned Gene

For base sequencing of the gene cloned in the recombinant vector (pET20-xylC) in Example 1, the recombinant vector was cut with various enzymes on the basis of the gene maps of two vectors M13 mp18 and M13 mp19. DNA fragments thus obtained were subcloned into M13 mp18 and M13 mp19 and then subjected to base sequencing analysis in the presence of AmpliTaq DNA polymerase with the aid of an ABI PRISM BigDye primer cycle-sequencing kit (Perkin-Elmer, USA). In order to read the two strands of the DNA of interest in both directions, nucleotide fragments were partially synthesized. Through comparison with the base sequence from GenBank, the cloned DNA was determined to be the xylC gene.

EXAMPLE 3

Preparation of Transformant Expressing BZDH

Using a calcium chloride method (refer to: Sambrook et al., Molecular Cloning, A Laboratory Manual 2nd Ed., Cold Spring Harbor Laboratory Press, Cold Spring Harbor, N.Y., 1989), *E. coli* XL1-Blue was transformed with the pET20-xylC vector, and grown on an LB plate (yeast extract, 5 g/L; Trypton, 10 g/L; NaCl, 10 g/L) supplemented with ampicillin (100 mg/L), X-gal, IPTG and bacto-agar (15 g/L) to select transformed *E. Coli* XL1-Blue (pET20-xylC).

EXAMPLE 4

Expression of xylC Gene

To examine the expression of the xylC gene in the transformed microorganism, the transformant XL1-Blue(pET20-xylC) obtained in Example 3 and the wild type XL1-Blue as a control were cultured in the same conditions and the benzaldehyde dehydrogenase expressed from each kind of bacteria was measured for activity. In this regard, the transformant of Example 3 and the control were inoculated in respective LB media, cultured at 37° C. for sufficient time, and then in 100 ml of LB media in an amount of 1% (v/v). When absorbance at 600 nm reached 0.4 to 0.5, 0.5 mM of IPTG was added to induce the expression of xylC, followed by incubation at 37° C.

EXAMPLE 5

Conversion from 2-Formyl-6-naphthoic acid (FNA) into 2,6-Naphthalene Dicarboxylic Acid (NDA) Using Expressed BZDH Cell mass was recovered by centrifuging the culture of the microorganism that expressed benzaldehyde dehydrogenase in Example 4, washed with 0.85% physiological saline and incubated with the reaction solution of Table 1 in a 30° C. tank for 6 hours, followed by high performance liquid chromatography (HPLC) analysis. In the reaction solution of Table 1, the pH of the buffer was set at 8.0, the concentration of DMSO at 5%, and the content of FNA in NDA at 9%.

Analysis results are given in Table 2, below. As seen in Table 2, the transformant XL1-Blue (pET20-xylC) was far superior to the wild type in ability to convert FNA into NDA. The HPLC analysis was performed under the conditions set in Table 3, below.

TABLE 1

| Composition | Amounts | Note |
| --- | --- | --- |
| 0.1M $KH_2PO_4$/KOH (pH 8.0) | 42.5 ml | |
| Glucose | 0.25 g | Final Conc: 0.5% |
| DMSO | 0.5 ml | |
| NDA solution (100 mg/ml DMSO) | 2.0 ml | DMSO Final Conc: 5% FNA Content in NDA: 9% |
| Cell Suspension | 5.0 ml | |
| Total | 50 ml | |

TABLE 2

| Cells | Rxn Time (hr) | FNA (Relative %) | NDA (Relative %) |
|---|---|---|---|
| XL1-Blue (pET20-xylC) | 0 | 100.0 | 100.0 |
| | 1 | 96.2 | 100.0 |
| | 3 | 77.3 | 102.4 |
| | 6 | 65.2 | 104.0 |
| XL1-Blue | 0 | 100.0 | 100.0 |
| | 1 | 99.9 | 100.0 |
| | 3 | 99.8 | 100.0 |
| | 6 | 99.9 | 100.0 |

TABLE 3

| HPLC | LC10-ADVP(Shimadzu) | |
|---|---|---|
| Column | Xterra ™ RP18 (4.6 × 250 mm, Waters) | |
| Detector | UV 240 nm | |
| Column Temp. | 40° C. | |
| Flow Rate | 1 ml/min | |
| Injection Volume | 20 μl | |
| Mobile Phase | Time (min) | 0.3% Phosphoric Acid | Acetonitrile |
| | 0 | 98 | 2 |
| | 5 | 92 | 8 |
| | 28 | 52 | 48 |
| | 30 | 20 | 60 |
| | 35 | 5 | 95 |
| | 36 | 98 | 2 |
| | 49 | 98 | 2 |

INDUSTRIAL APPLICABILITY

As described hereinbefore, the transformant prepared in accordance with the present invention is greatly effective in removing 2-formyl-6-naphthoic acid from crude naphthalene dicarboxylic acid. Therefore, the method of the present invention can be used to produce highly pure 2,6-naphthalene dicarboxylic acid in an economically favorable and environmentally friendly manner, providing high industrial applicability.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for purifying crude naphthalene dimethylcarboxylic acid, comprising: reacting crude naphthalene dimethylcarboxylic acid with a transformant, prepared by constructing a recombinant expression vector carrying the gene of SEQ ID NO:1 encoding benzaldehyde dehydrogenase (xylC) obtained from Sphingomonas aromaticivorans KCTC 2888, and transforming an E. coli host cell with the recombinant expression vector; wherein the reacting of the crude naphthalene dimethylcarboxylic acid with the transformant results in the conversion of 2-formyl-6-naphthoic acid contained within the crude naphthalene dimethylcarboxylic acid into 2,6-naphthalene dicarboxylic acid.

2. The method as set forth in claim 1, wherein the reaction of the crude naphthalene dimethyl carboxylic acid with the transformant is carried out in a buffer solution containing 0 to 20% of an organic solvent, the organic solvent being selected from a group consisting of dimethyl sulfoxide, dimethyl formamide, dimethyl acetamide and tetrahydrofuran.

3. The method as set forth in claim 1, wherein the reaction is carried out at from 25 to 45° C. for 0.5 to 48 hours.

4. The method as set forth in claim 1, wherein the crude naphthalene dimethylcarboxylic acid is reacted with the transformant in a buffer solution containing an organic solvent, the buffer solution being a potassium phosphate solution and ranging from 6.0 to 10.0 in pH.

* * * * *